April 9, 1963 TAKEO YUGE ETAL Plant Pat. 2,249

AZALEA PLANT

Filed Feb. 20, 1961

INVENTORS
TAKEO YUGE
KANJI K. YUGE

BY Spensley and Horn
ATTORNEYS

United States Patent Office

Plant Pat. 2,249
Patented Apr. 9, 1963

2,249
AZALEA PLANT

Takeo Yuge and Kanji Kay Yuge, both of
177 E. Mariposa St., Altadena, Calif.
Filed Feb. 20, 1961, Ser. No. 90,611
1 Claim. (Cl. 47—60)

This invention relates to a new and distinct variety of azalea plant characterized particularly by its early and extended blooming season and its bright crimson red flowers with orange undertones which are produced profusely on a plant of fine, uniformly compact growth habit. The present variety commences blooming in January and remains heavily in bloom through February with flowers that are long lasting with no fading or color change as the flowers age. Each of the flowers will last at least three to fuor weeks and the flowers are very large double reds with very dark red spots or speckles on the petals. The plant has flowers larger than known varieties of red azalea which bloom in January.

This variety of azalea plant was produced in the experimental garden of the applicants' nursery at Altadena, California; the variety being the result of a cross between a Belgian semi-double unpatented variety known as Miss Cottage Gardens and a Belgian Indica azalea being a selected double seedling of the inventors known as Kaho, a variety which is unpatented. This cross pollination was carried out in the applicants' nursery at Altadena, California, in February 1950, the seeds resulting from the cross pollination were collected in November 1950 and planted in March 1951. The seedlings produced in this manner were observed over an extended period of time and this particular variety was selected and segregated.

Upon the cross being recognized as novel, and particularly when the unusual flower size and color of the variety was found, it was taken for propagation by cuttings at the aforesaid nursery in Altadena, California, and such cuttings produced azalea plants which carried forward all of the new and distinct features of the subject original plant. Subsequent propagation of the variety by cuttings further evidenced that the variety is fixed in its floricultural characteristics.

In the accompanying illustration:

Figure 3:
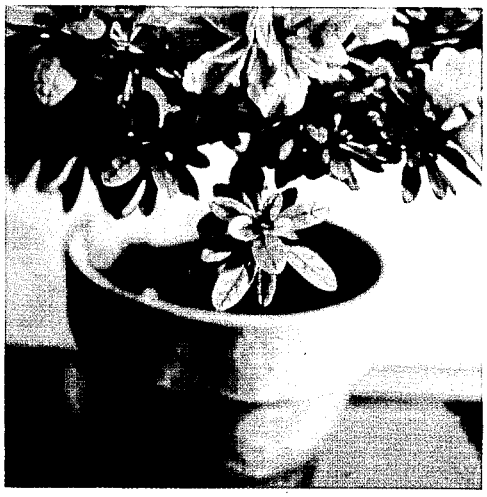
Figure 2:
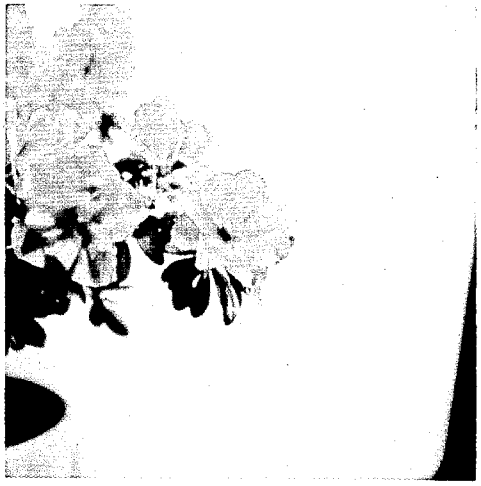
FIGURE 2 is a perspective view of a stem, with leaves and flowers.
Figure 1:
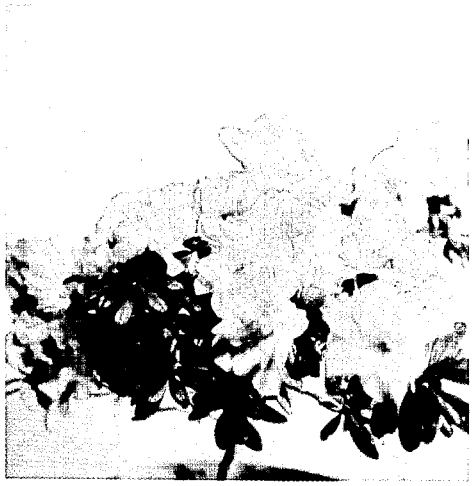
FIGURE 1 is a perspective view showing the flowers in bloom.

Referring now more specifically to the botanical details of the new and distinct variety of azalea plant of the present invention, the following is an outline description of the same:

*Plant*

Form: Many branched, rounded, symmetrical form.

Growing habit: Dense and bushy with heavy glossy green foliage. The rate of growth is rapid and more rapid than most prior Belgian varieties.

Blooming habit: Flowers bloom out evenly over the entire plant when forced in the greenhouse or flowered naturally in the garden. Usually two to five separate flowers blossom from each bud produced on each stem.

Blooming season: January through February in southern California without forcing or heating.

Foliage:

*Size.*—Mature foliage 1¾" to 2" long and ½" to ⅝" in width.

*Color.*—Deep green.

*Shape.*—Elliptic with slightly mucronate tip. Revolute. Concave on bottom side.

*Aspect.*—Glossy with some hairs on both sides. Slightly pubescent.

*Texture.*—Medium.

*Edges.*—Entire—not serrated.

*Ribs and veins.*—Six to seven branch veins leading off main center vein, multiple veins leading off the branch veins. Pinnately veined.

*Flower*

Size: Average 3½" to 4" in diameter by 2" in length, buds are short and stout.

Borne: 2 to 5 each stem.

Stem: Medium length with sufficient strength to hold the flowers properly.

Form: Double, ruffled petals. Almost perfectly cyclic; i.e., regular—especially the bud form.

Permanence: Long lasting without fading or changing color as flowers age. Flowers last average of three to four weeks in southern California.

Petalage: Six outer petals with 9 to 10 inner petals.

Color: Crimson red. (See chart below.)

Petals:

*Texture.*—Thick and heavy.

*Appearance.*—At least one-half of the petals have very dark red speckles.

*Shape.*—Inside petals consist of a definite center fold with the petals lying outwardly.

*Arrangement.*—Cyclic—almost perfect.

*Persistence.*—Remains firm without wilting or color change until flower falls.

Reproductive organs:

*Stamens.*—0 to few. (Occasional.)

*Ovaries.*—Normal.

The color designations according to "A Dictionary of Color" by Maerz and Paul are as follows:

| Part | Color | Plate | Letter | Number |
|---|---|---|---|---|
| Foliage: | | | | |
| New Leaves | Art Green | 22 | L | 7 |
| Mature Leaves | | 23 | E | 12 |
| Stems (New Growth) | Kazak Coptic | 7 | L | 9 |
| Flower: | | | | |
| Outer edge of Petals | Chianti Antique Ruby. | 6 | L | 6 |
| Base of Petals | | 4 | K | 5 |

Having thus disclosed our invention, we claim:

The new and distinct variety of azalea plant substantially as herein shown and described, being a cross between a Belgian semi-double variety known as Miss Cottage Gardens and a Belgian double, Kaho, and characterized by the large size and bright red color of its flowers.

No references cited.